United States Patent [19]

Shinozaki

[11] Patent Number: 5,448,916

[45] Date of Patent: Sep. 12, 1995

[54] METHOD AND DEVICE FOR THREE DIMENSIONAL MEASURING OF SURFACE

[75] Inventor: Mamoru Shinozaki, Tokyo, Japan

[73] Assignee: Takenaka Corporation, Osaka, Japan

[21] Appl. No.: 165,529

[22] Filed: Dec. 13, 1993

Related U.S. Application Data

[63] Continuation of Ser. No. 931,386, Aug. 18, 1992, abandoned.

[30] Foreign Application Priority Data

Apr. 30, 1992 [JP] Japan ................... 4-111443

[51] Int. Cl.6 ................................. G01V 1/40
[52] U.S. Cl. ........................ 73/597; 73/619; 73/620; 73/623; 181/105; 367/27; 367/35
[58] Field of Search ............... 73/620, 621, 622, 623, 73/597, 598, 594, 618; 181/102, 104, 105, 103; 367/25, 27, 35, 86, 30, 31, 69; 346/107 W

[56] References Cited

U.S. PATENT DOCUMENTS

| | | | |
|---|---|---|---|
| 2,989,864 | 6/1961 | Bamford | 073/620 |
| 3,511,334 | 5/1970 | Zemanek, Jr. | 181/104 |
| 3,614,891 | 10/1971 | Nolte | 181/104 |
| 4,014,207 | 3/1977 | Meyer et al. | 073/621 |
| 4,140,954 | 2/1979 | Jeffras et al. | 073/619 |
| 4,370,889 | 2/1983 | Ruthrof et al. | 073/619 |
| 4,399,822 | 8/1983 | Theumer | 073/633 |
| 4,524,433 | 6/1985 | Broding | 181/105 |
| 4,780,858 | 10/1988 | Clerke | 181/105 |
| 4,829,488 | 5/1989 | Sigfried, II | 181/105 |

FOREIGN PATENT DOCUMENTS

| | | |
|---|---|---|
| 495726 | 2/1974 | Japan . |
| 5014961 | 5/1975 | Japan . |
| 557525 | 2/1980 | Japan . |

Primary Examiner—Hezron E. Williams
Assistant Examiner—Nashmiya Ashraf
Attorney, Agent, or Firm—Ronald P. Kananen

[57] ABSTRACT

A measuring technique for producing a three-dimensional image and information relating to the type of sand, clay or gravel which defines a wall or walls of a deep concealed underground excavation which is filled with a stabilizing liquid, and which technique facilitates accurate and safe construction, utilizes a transducer which irradiates a surface of the excavation with ultrasonic waves and detects the waves which are reflected back thereto. The transducer scans horizontally in incremental stages which occur with a predetermined angle pitch. After each scan is completed, the transducer is vertically displaced by a predetermined amount and the horizontal scan is repeated. The time required for a wave to reach and be reflected back to the transducer is used to determine the distance of the wall from the device. This is used in combination with data indicative of the horizontal and vertical positions of the device to enable the shape of the surface to be determined and for qualitative data such as the type of material from which the wall is composed, to be determined from the patterns produced by the received waves.

5 Claims, 4 Drawing Sheets

METHOD AND DEVICE FOR THREE DIMENSIONAL MEASURING OF SURFACE

This is a continuation of application Ser. No. 07/931,386 filed Aug. 18, 1992 now abandoned.

BACKGROUND OF THE INVENTION

During the construction of an underground concrete diaphragm wall or an in-situ concrete pile, it is very important to be able to ascertain details of a wall surface condition which is stabilized using liquid, in the form of visual images for maintaining the quality of construction as well as for safety purposes. In this connection measuring devices which utilize ultrasonic waves have been both disclosed and put into practical application. Examples of these methods are disclosed in Japanese Patent Application No. 49-5726 (Registered Patent No. 1059047), No. 50-14961 (Registered Patent No. 1119189) and No. 55-7525.

The above-mentioned conventional measuring devices which utilize ultrasonic waves, however, can only achieve two-dimensional measuring of, so to speak, vertical sections of a deep trench or a deep hole and enable a two-dimensional visualization of the wall configuration, inclination and surface irregularity, and cannot provide three-dimensional surface information. Further, conventional measuring devices cannot provide information relating to the quality of the surface which reflects the ultrasonic waves (the kind of stratum, for example, that constitutes the wall surface) and hence cannot indicate if an irregularity of the surface is caused by clay being swelled by water or by mechanical deformation. Thus, these devices are quite inadequate as measuring devices and cannot provide the information necessary for judgments which are essential for maintaining construction quality and necessary safety levels.

SUMMARY OF THE INVENTION

In accordance with the present invention, a measuring technique for producing a three-dimensional image and information relating to the type of sand, clay or gravel which defines a wall or walls of a deep, concealed underground excavation which is filled with a stabilizing liquid, and which technique facilitates accurate and safe construction, utilizes a transducer which irradiates a surface of the excavation with ultrasonic waves and detects the waves which are reflected back thereto. The transducer scans horizontally in incremental stages which occur with a predetermined angle pitch. After each scan is completed, the transducer is vertically displaced by a predetermined amount and the horizontal scan is repeated. The time required for a wave to reach the surface and be reflected back to the transducer is used to determine the distance of the wall from the device. This is used in combination with data indicative of the horizontal and vertical positions of the device to enable the three-dimensional shape of the surface to be determined and for qualitative data, such as the type of material from which the wall is composed, to be determined from patterns derived using the received waves.

A three-dimensional measuring device according to the present invention is designed to measure a concealed surface of an underground excavated void which is filled with a stabilizing liquid, comprising: a) a transducer which irradiates the surface with ultrasonic waves and which is equipped with means for receiving waves reflected by the surface; b) an oscillator which excites ultrasonic waves in the transducer; c) a rotation-support device which (a) orients the transducer toward the wall surface under liquid and rotates the transducer horizontally for scanning through a prescribed angle range in increments which have a predetermined pitch, and (b) which shifts the transducer vertically in increments which have a predetermined pitch, after each full horizontal scanning of the transducer; (d) a direction-position controller which drives and controls the rotation-support device; and (e) a processing unit which receives signals indicative of the emitted and reflected waves from the transducer, signals from the direction-position controller which controls the rotation-support device and the vertical support device, processes these signals and then records and displays, as visual image data, information indicative of wall position, wall configuration and qualitative data indicative of the material from which the wall surface is formed.

The oscillator excites vibration of the frequency range of, for example 200–500 kHz in said transducer. To monitor waves generated by said oscillator, the oscillator is connected to a trigger terminal of a synchroscope.

The rotation-support device is horizontally rotated through an angle pitch or increment of, for example, 0.9 degree, which corresponds to the width of a picture element, by a stepping motor which is driven and controlled by the direction-position controller. The transducer executes another scanning cycle by emitting and receiving ultrasonic waves. In each position, the horizontal position indicative signal from the direction-position controller which is counted in the pitch angles, and emitted and received waves from the transducer, are input to a personal computer included in the processing unit.

The vertical support device vertically displaces the transducer by increments having a pitch of, for example, 7 mm during the return stage of said transducer and after each completion of a full horizontal scanning to the original position thereof. The vertical position indicative signal sent out at this time by said direction-position controller corresponding to the present pitch number is also fed into said processing unit. In brief, the standards of direction and position whereby said transducer is driven and controlled, and hence the coordinates of the points of three-dimensional surfaces are determined, at will by the values input to said direction-position controller by way of, for example, a floppy disk on which said values are stored.

The processing unit generates matrixes (coordinates of the three-dimensional surface points) by composing the signals, received as described above, of the horizontal direction and position, and of the vertical position. Further, by superimposing the information signals indicative of emitted and received waves, the position and configuration of the surface and the qualitative information the surface material are rendered visualizable. More specifically:

(1) From the time difference (t in FIG. 4D) of the ultrasonic waves emitted and received by said transducer, information indicative of distance and irregularity of the surface is obtained;

(2) The reflected waves received at each position (position on the scanning lines of the transducer) are saved for each interval as shown in FIG. 5 by scanned lines I and II, and, from variations in the waves patterns, information which enables the identification of the wave-reflecting matter (viz., the material constituting the wall surface; e.g., loam, silt, clay, etc.). To make the above possible, wave patterns corresponding to walls consisting of specific material such as silt, sand clay, etc. are cataloged into the processing unit and the waves which are obtained are compared for similarity with cataloged patterns and the results are visualized and expressed as colored and shaded images.

According to the three-dimensional measuring method and device of the present invention, information relating to the configuration and quality of a wall surface which is invisible under stabilizing liquid, can be recorded and displayed as three-dimensional images which provide accurate and sufficient judgment material for maintaining construction quality and safety control.

DETAILED DESCRIPTION OF THE PREFERRED EMBODIMENT

Figure 1:
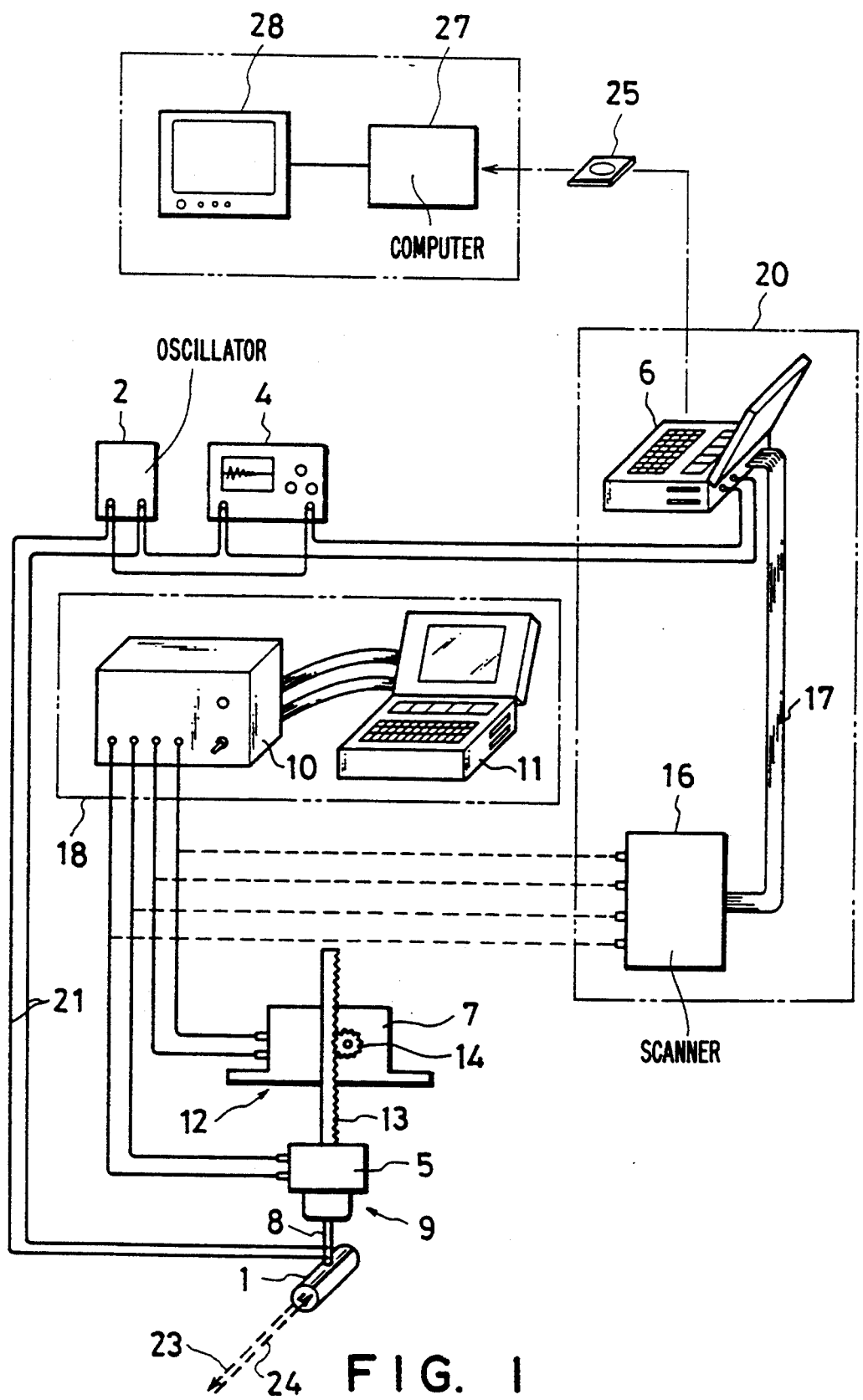
FIG. 1 is a system diagram showing an embodiment of a three-dimensional surface measuring device according to the present invention.
Figure 6:
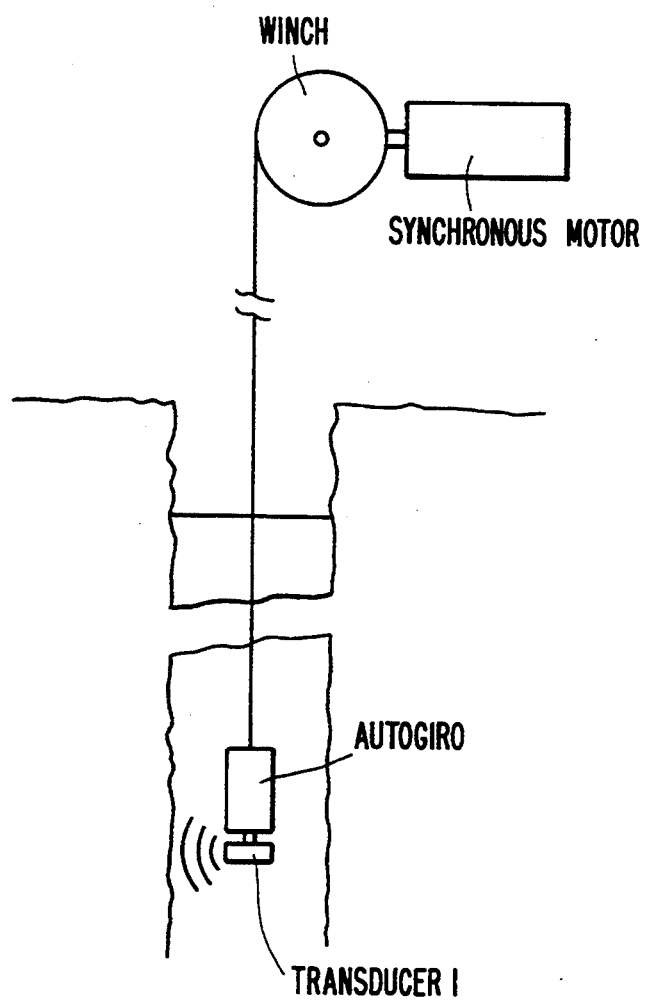
FIG. 6 is a sketch showing the invention used in conjunction with a winch.

FIG. 1 shows, as a system diagram, a structure of a three-dimensional measuring device of surfaces. In the three-dimensional measuring device shown in FIG. 1, an oscillator 2 that excites ultrasonic waves of 200–500 kHz in a transducer 1, is connected to the transducer 1 by one of a pair of cables 21 and to trigger terminals of the oscillator 2 and a synchroscope 4 for monitoring emitted and received waves. The trigger terminals are also connected to a personal computer 6 of a processing unit 20. The transducer 1 is supported by a vertical elongate shaft 8 for horizontal scanning movement and is connected to a shaft of a stepping motor 5 included in a rotation-support device 9 which produces the required horizontal rotation. The stepping motor 5 is connected through an interface 10 of a direction-position controller 18 to a control unit 11 (personal computer). By this direction-position controller 18, the transducer 1 is turned horizontally through increments having a pitch of, for example, 0.9 degree. The direction-position controller 18 includes a direction-position signal system to turn the transducer 1 horizontally 56 increments on each side of a zero line 15 (viz., center line; see FIG. 2) for scanning in the event, for example, the range of scanning of the transducer 1 is 100.8 degrees. The stepping motor 5 is supported vertically by a rack 13 which forms part of a vertical support device 12. The vertical support device 12 is provided in such a manner as to be vertically displaceable by a predetermined increment by a rack-pinion mechanism wherein a pinion which engages with said rack 13, is driven for rotation by a stepping motor 7. This stepping motor 7 is also connected to the control unit 11 of the direction-position controller 18 through the interface 10. The stepping motor 7 is driven and controlled by the direction-position controller 18 to lift or lower (vertically displace) said transducer 1 by increments having a pitch of, say, 7 mm after each full horizontal rotation in the prescribed scanning range (a turn of 100.8 degree in this embodiment) of said transducer 1 by said rotation-support device 12 which can be implemented by the rack-pinion mechanism is only a few meters. Accordingly, it is a common practice, for a greater depth range, to suspend the transducer 1 on a winch (see FIG. 6) and to control vertical position thereof through coupling of said winch and a synchronous motor while the origin (zero line) of horizontal rotation is determined by an autogiro. In either case, the transducer 1 is driven and controlled with respect to direction and position (position on the scanning lines) in accordance with a coordinate system set, so as to scan the wall surface 3 under inspection and the data input to the direction-position, controller 8 from a floppy disk. When the surface under inspection is of a hole for a pile, it is advantageous to set the horizontal scanning angle range at 360 degrees. When the surface is a flat plane such as of a trench, information of the whole surface can be obtained by repeating measurement along the surface with a horizontal scanning range which is restricted to about 100 degrees.

Figure 4:
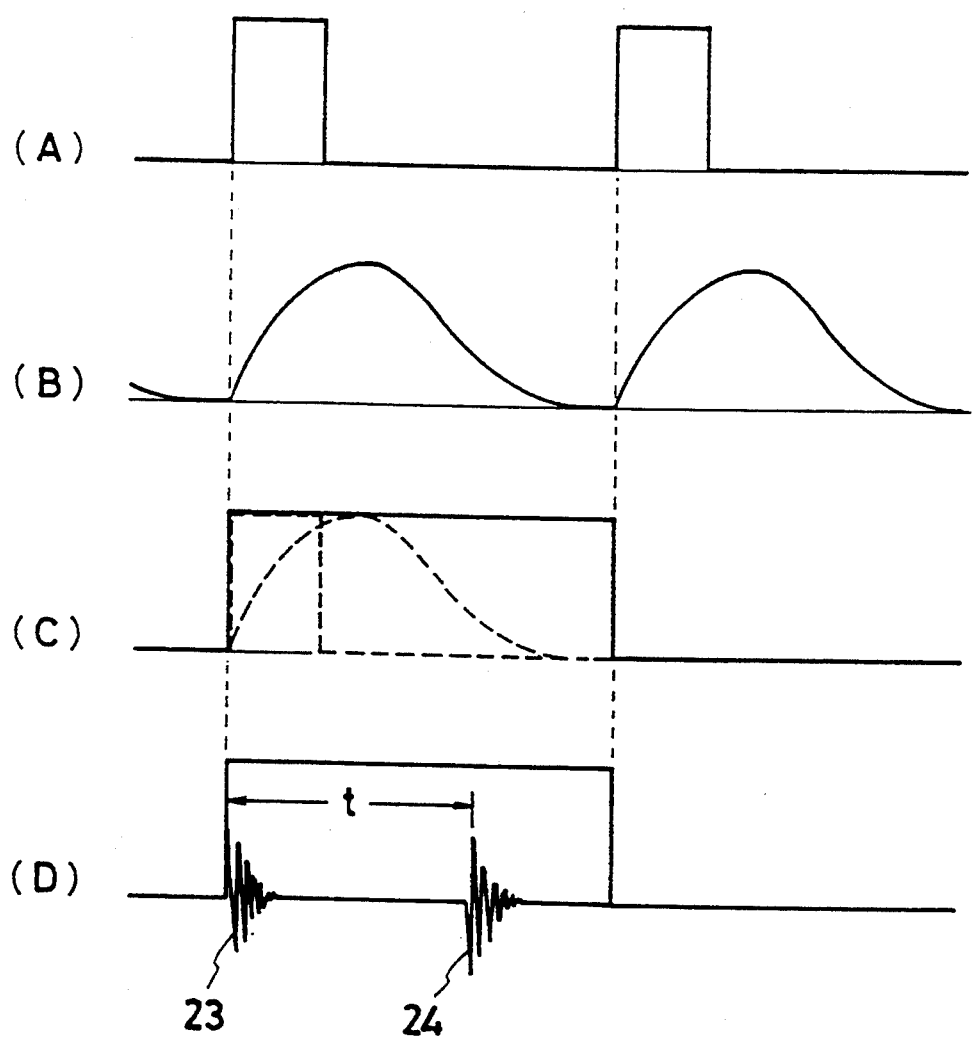
FIG. 4 A-D are graphs showing examples of the relationship between the emitted and received waves.
Figure 5:
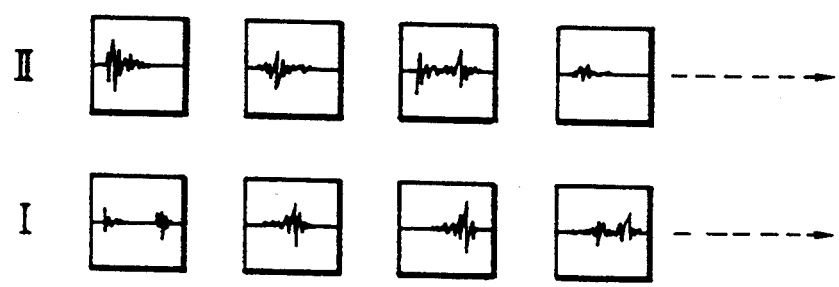
FIG. 5 is a set of monitored waves patterns which are produced by scanning lines I and II at consecutive time intervals.

The transducer 1 repeats the cycle of remitting ultrasonic waves and receiving the reflected waves (FIG. 4B) from the wall surface 3 for each pitch of the horizonal rotation (FIG. 4A). Thus, with the above described example, the transducer 1 cyclically repeats emission and reception of ultrasonic waves for the scanning angle range of 100.8 degrees 56 times for each of the positive and negative sides; viz., 112 times in total. These emitted waves 23 and received waves 24 (FIG. 4D) are fed into the personal computer 6 of a processing unit 20. This input to the personal computer 6 can be carried out either for each increment or for each stroke wherein all of the stored data of 112 steps of a full horizontal scanning are temporarily stored. The direction-position control signals (coordinates of a three-dimensional surface) of the transducer 1 sent out by the direction-position controller 11 and received by the scanner 16, the emitted waves 23 from the transducer 1 and the received waves 24 which bring about information of configuration (including roughness and inclination) and material of the surface 3, are processed and synthesized in the personal computer 6 and recorded on a floppy disk 25 as visual data. Therefore, as the floppy disk 25 taken out of the personal computer is set in a computer 27 for visualization processing, information of position, configuration and quality of the wall surface can be displayed on a monitor as three-dimensional images for visual inspection.

Figure 2:
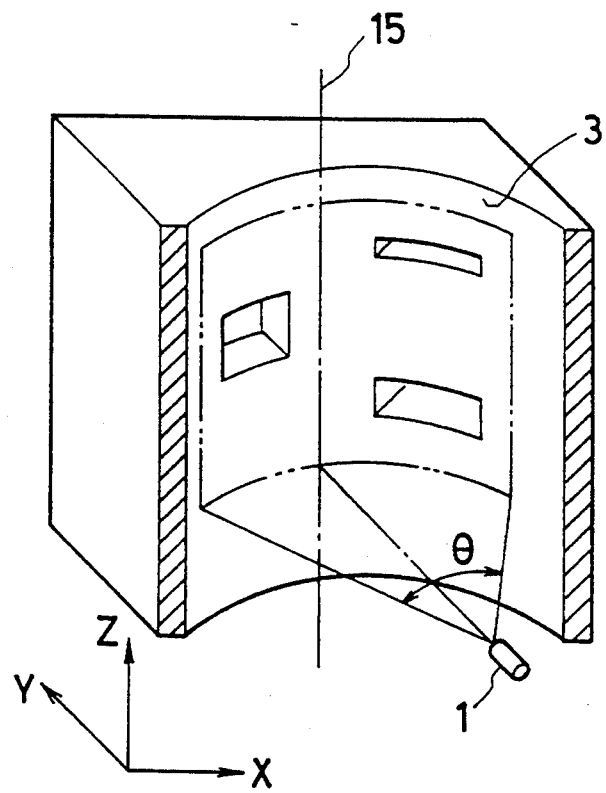
FIG. 2 is an illustration showing the method by which the surfaces are three-dimensionally measured.
Figure 3:
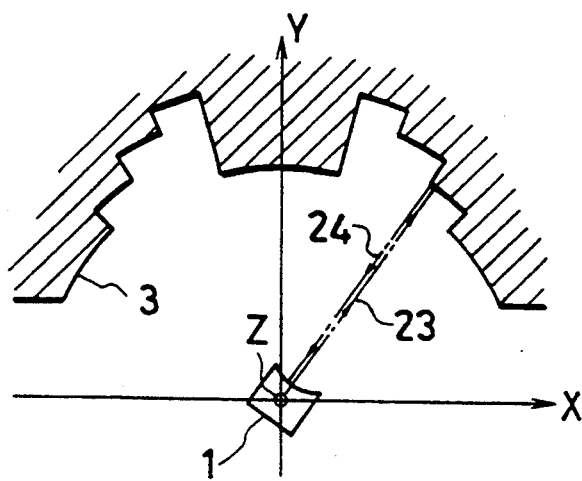
FIG. 3 is another illustration of the three-dimensional surfaces measuring method utilized in the present invention.

The operation of the above described three-dimensional measuring device can be summarized based on FIG. 2 and FIG. 3 as follows:

(1) The depth Z of the transducer 1 is set to the measuring position by manual operation of the vertical support device 12. The value of said position is reset to zero as an origin.

(2) A vertical-central line 15 on the wall surface of a deep trench or a deep hole is taken as the origin, and the range of horizontal rotation angle of the transducer 1 on the X-Y plane is determined with the direction-position controller 11. Further, the pitch value and the number of increments for the horizontal scanning are set. Still further, the vertical pitch value is determined.

(3) After the above, overall operation of the system is indicated and three-dimensional measurement of a wall surface 3 begins.

What I claim:

1. A three-dimensional surface measuring method for a concealed surface of a deep underground excavated void which is filled with a stabilizing liquid, said excavated void having a wall surface, comprising the steps of:

turning a transducer, which irradiates ultrasonic waves against said wall surface of the liquid filled underground excavated void and which is equipped with means for receiving waves which are reflected from said wall surface, through a prescribed angle range about a generally vertical amid in incremental stages which have a predetermined pitch;

repeating a cycle of irradiation and reception of waves at each incremental stage while measuring a time difference in wave propagation so as to horizontally scan said wall surface;

collecting and recognizing wave patterns of said ultrasonic waves which are reflected off of the wall surface and received by said transducer, and comparing said wave patterns with known wave patterns of other wall compositions, which known wave patterns and related data have been previously catalogued;

shifting said transducer vertically in increments which have a predetermined pitch after each turning of said transducer through said prescribed angle range; and deriving, for visualization and display, data relating to a distance of said wall surface from said transducer, wall surface configuration, and qualitative data relating to a material from which said wall surface is formed using wave propagation time differences, recognized patterns of the reflected waves received by said transducer, and signals designating the horizontal position and the vertical position of said transducer.

2. A three-dimensional measuring device for a concealed surface of an underground excavated void which is filled with a stabilizing liquid, said surface forming part of said excavated void, comprising:

a) a transducer which irradiates said surface with ultrasonic waves and which is equipped with means for receiving waves reflected by said surface;

b) an oscillator which excites ultrasonic waves in said transducer;

c) a rotation-support device which (a) orients said transducer toward said wall surface under liquid and rotates said transducer about a generally vertical axis for scanning through a prescribed angle range in increments which have a predetermined pitch, and (b) which shifts said transducer vertically in increments which have a predetermined pitch after each rotation of said transducer through said prescribed angle range;

(d) a direction-position controller which drives and controls said rotation-support device; and (e) a processing unit which receives signals indicative of the emitted and reflected waves from said transducer and signals from said direction-position controller indicative of a vertical and angular position of said transducer, processes these signals to determine a time difference in wave propagation and a wave pattern at each position of the transducer, compares the wave patterns with known wave patterns of other wall compositions which have been previously stored in said processing unit, and then records and displays, as visual image data, information indicative of wall position, wall configuration and qualitative data indicative of the type of material from which the wall surface is formed.

3. A three-dimensional measuring device for a surface of an underground excavated void which void is filled with a stabilizing liquid, said surface forming part of said void, comprising:

transducer means for irradiating said surface with ultrasonic waves and for receiving waves reflected by said surface, said transducer being operatively connected with an oscillator which excites ultrasonic wave emission from said transducer;

suspension means for suspending said transducer in said excavated void;

scanning means operatively connected between said suspension means and said transducer for orienting said transducer toward said surface and for incrementally rotating said transducer about a generally vertical axis through a predetermined angle;

control means which is operatively connected with said suspension means and with said scanning means for inducing said suspension means to incrementally displace said transducer in a vertical direction each time said scanning means completes incrementally rotating said transducer through said predetermined angle; and data processing means operatively connected with said transducer and said control means for receiving signals from said transducer and said control means for measuring a time difference in wave propagation and a wave pattern at each position of said transducer, for comparing said wave patterns with known wave patterns of other wall compositions that have been previously catalogued, and for producing a three-dimensional image of said surface which indicates the material from which said surface is formed.

4. A three-dimensional measuring device as set forth in claim 3, wherein said suspension means comprises a winch and wherein said scanning means comprises an autogiro.

5. A three-dimensional surface sensing method for simultaneously measuring the configuration and determining the composition of a concealed wall surface of an underground void which is filled with a stabilizing liquid, comprising of the following steps:

turning a transducer about a generally vertical axis within said underground void through a prescribed angle range in incremental stages of a predetermined degree;

emitting ultrasonic waves directed at said wall surface and receiving such waves after reflection off said wall surface at each incremental stage;

shifting said transducer vertically within said underground void in increments of a predetermined height after each full turning of said transducer through said prescribed angle range, followed by further turning of said transducer and emission and reception of said ultrasonic waves as described above;

measuring by wave propagation time differences of the distance of said wall surface from said transducer and the configuration of said wall surface at each point measured;

simultaneously with the above step, collecting and recognizing the wave patterns of said ultrasonic waves which are reflected off said wall surface and received by the transducer and comparing said wave patterns with known wave patterns of other wall compositions, which known wave patterns and related data have been previously cataloged; and storing and displaying the data obtained as described above so as to indicate the configuration of the wall surface and the composition of said wall surface for the area measured.

* * * * *